US011185343B2

(12) United States Patent
Walberg et al.

(10) Patent No.: US 11,185,343 B2
(45) Date of Patent: Nov. 30, 2021

(54) SURGICAL INSTRUMENT HAVING IMPROVED CLOSING CHARACTERISTICS

(71) Applicant: AESCULAP AG, Tuttlingen (DE)

(72) Inventors: Erik Walberg, Tuttlingen (DE); Eugen Herner, Villingen-Schwenningen (DE)

(73) Assignee: AESCULAP AG, Tuttlingen (DE)

( * ) Notice: Subject to any disclaimer, the term of this patent is extended or adjusted under 35 U.S.C. 154(b) by 37 days.

(21) Appl. No.: 16/611,005

(22) PCT Filed: May 9, 2018

(86) PCT No.: PCT/EP2018/062010
§ 371 (c)(1),
(2) Date: Nov. 5, 2019

(87) PCT Pub. No.: WO2018/206648
PCT Pub. Date: Nov. 15, 2018

(65) Prior Publication Data
US 2020/0078034 A1 Mar. 12, 2020

(30) Foreign Application Priority Data
May 9, 2017 (DE) ..................... 10 2017 109 891.7

(51) Int. Cl.
A61B 17/29 (2006.01)
A61B 18/14 (2006.01)
A61B 90/00 (2016.01)

(52) U.S. Cl.
CPC ...... A61B 17/2909 (2013.01); A61B 18/1445 (2013.01); A61B 2017/292 (2013.01); A61B 2017/2902 (2013.01); A61B 2090/035 (2016.02)

(58) Field of Classification Search
CPC .... A61B 2017/2912; A61B 2017/2913; A61B 2017/2918; A61B 2017/2919;
(Continued)

(56) References Cited

U.S. PATENT DOCUMENTS 4,909,789 A 3/1990 Taguchi et al.
9,782,188 B2 10/2017 Stefan et al.
(Continued)

FOREIGN PATENT DOCUMENTS

DE 293929 C 9/1916
DE 3709706 A1 10/1987
(Continued)

OTHER PUBLICATIONS

International Search Report and Written Opinion for International Application No. PCT/EP2018/062010, dated Sep. 25, 2018, 15 pages.
(Continued)

Primary Examiner — Majid Jamialahmadi

(57) ABSTRACT

A surgical instrument includes an instrument shaft, two instrument branches that can be positioned relatively to one another in a working position and a rest position, a handle element on which an operating element is movably arranged for positioning the instrument branches, and a coupling mechanism having a translating unit that converts a movement of the operating element, non-linearly, into a relative movement of at least one of the two instrument branches. The coupling mechanism includes at least one bias element that biases the mechanism into the rest position and/or into the working position of the instrument branches.

13 Claims, 8 Drawing Sheets

(58) Field of Classification Search
CPC .... A61B 2017/2924; A61B 2017/2901; A61B 2017/2902; A61B 2017/2922; A61B 2017/292; A61B 17/2812; A61B 17/2909; A61B 17/29

See application file for complete search history.

(56) References Cited

U.S. PATENT DOCUMENTS

| | | |
|---|---|---|
| 10,398,496 B2 | 9/2019 | Rothweiler et al. |
| 2006/0217697 A1 | 9/2006 | Lau et al. |
| 2012/0184988 A1* | 7/2012 | Twomey ............ A61B 17/2909 606/205 |
| 2014/0155933 A1 | 6/2014 | Stefan et al. |
| 2015/0282866 A1 | 10/2015 | Rothweiler et al. |
| 2016/0331396 A1 | 11/2016 | Schweitzer et al. |

FOREIGN PATENT DOCUMENTS

| | | |
|---|---|---|
| DE | 29713490 U1 | 10/1997 |
| DE | 102012110660 A1 | 5/2014 |
| DE | 102014100603 A1 | 7/2015 |
| EP | 2732778 A1 | 5/2014 |
| EP | 3095399 A2 | 11/2016 |
| JP | 2000175927 A | 6/2000 |
| WO | 9515124 A1 | 6/1995 |
| WO | 9851179 A1 | 11/1998 |
| WO | 2006071121 A1 | 7/2006 |

OTHER PUBLICATIONS

German Search Report for German Application No. 10 2017 109 891.7, with English Translation, dated Feb. 26, 2018, 17 pages.

* cited by examiner

SURGICAL INSTRUMENT HAVING IMPROVED CLOSING CHARACTERISTICS

CROSS-REFERENCE TO RELATED APPLICATIONS

This application is the United States national phase entry of International Application No. PCT/EP2018/062010, filed May 9, 2018, which claims the benefit of priority of German Application No. 10 2017 109 891.7, filed May 9, 2017. The contents of International Application No. PCT/EP2018/062010 and German Application No. 10 2017 109 891.7 are incorporated by reference herein in their entireties.

FIELD

The invention relates to a surgical instrument, particularly an electrosurgical instrument, comprising an instrument shaft, two instrument branches that are arranged distally thereupon and can be positioned relative to each another/moved between a working position and a rest position, and a handle element on which a manually actuatable operating element is movably arranged for positioning the instrument branches between the working position and the rest position. Examples of such instruments are clamps, forceps and RF instruments for the obliteration and/or coagulation of tissue.

BACKGROUND

For example, surgical instruments are known which enable body tissue to be gripped, held and clamped by means of a forceps-like or scissors-like tool to coagulate or to sever said body tissue by applying high-frequency voltage in a monopolar or bipolar manner. Instrument branches of the type of clamping jaws have to exert pressure on the tissue lying therebetween as intended. For obtaining a desired result of treatment, said pressure must be neither too high (destruction of tissue) nor too low (insufficient joining of tissue).

From DE 10 2012 110 660 A1, a surgical HF instrument comprising two tissue branches is known at least one of which is movable relative to the other and can be applied to the other tissue branch at a predetermined or predeterminable pressure via an actuating mechanism while clamping body tissue therebetween. The instrument includes a clamping pressure control means which is interconnected in a force or torque transmission train between the actuating mechanism and the at least one movable tissue branch.

Another important aspect in instruments of this type is the user friendliness. In this context, especially the actuating force to be applied by a user when making use of the instrument is mentioned. The instruments are to be precisely operated with low actuating forces in order to minimize fatigue of the user, as a rule of an operating surgeon, as well as possibly occurring side-effects such as trembling of the operating surgeon's hand that operates the instrument during lasting holding or with relatively high holding forces. Moreover, low actuating forces which are foreseeable to the user and thus do not take the user by surprise are beneficial to exact, precise and smooth handling of the instrument.

Finally, in minimally invasive surgery and, resp., endoscopy, especially laparoscopy, the optimization of space and weight of the surgical instruments used there plays an important role. Therefore, a space-saving and weight-saving design has to be considered not only for the distal instrument head but also for the proximal instrument handle actuated by the user.

SUMMARY

It is the object underlying the invention in view of this state of the art to provide a surgical instrument that improves the afore-described characteristics, can be used especially easily and by low actuating and holding forces and/or enables a preferably adjustable overload protection to prevent tissue damage and/or to protect the mechanism and mechanical components, respectively, against overload and/or has a simple structure, preferably of low weight and little space.

This object is achieved, according to the invention, by a surgical instrument, especially an electrosurgical instrument (RF instrument) comprising an instrument shaft, two instrument branches that are arranged distally thereupon and can be positioned relative to each another between a working position and a rest position, a handle element/handle portion on which an especially manually actuatable operating element is movably arranged for selectively positioning the instrument branches in the working position and the rest position, and a coupling mechanism having a translating unit that converts a movement of the operating element (due to user-side operation) non-linearly into a relative movement of at least one of the two instrument branches, wherein the coupling mechanism comprises or has an opening and/or closing actuating force supporting unit, preferably at least one bias element that at least temporarily biases the mechanism into the rest position (open position) and/or into the working position (closing position) of the instrument branches.

According to the invention, the instrument branches can be positioned relatively between the working position and a rest position. In the working position the instrument branches can be closed, then they are open in the rest position, for example in the case of a tissue clamp or a coagulation instrument. Alternatively, they can be open in the working position and closed in the rest position, for example in the case of a spacing instrument. While the instrument branches are arranged distally on the instrument shaft, the handle element is arranged or formed preferably proximally thereon. The handle element may be configured, according to the invention, as a handle, especially as a housing forming a handle. Alternatively, the handle element may be in the form of a robot arm and, resp., in the form of an interface for mechanically/hydraulically connecting a robot arm. In the handle element in the form of a housing, parts of the operating element, the transmission element, a spring element that will be mentioned in the further course of the description as well as the coupling mechanism or parts thereof can be accommodated, encased and supported.

The operating element can be arranged to be especially positioned and/or pivoted on the handle element, for example in the form of an actuating lever or slide. Preferably, it is operatively connected, on the one hand, to the handle element and, on the other hand, to the coupling mechanism. Preferably, the coupling mechanism or part of the coupling mechanism is positioned relative to the handle element, especially translationally positioned in the axial direction of the instrument shaft, by user-side actuation of the operating element.

The instrument branches at the distal ends of the shaft are arranged and intended to clamp and/or cut and/or energize tissue, particularly with high-frequency current for coagulating, obliterating or cutting the tissue.

The coupling mechanism is configured, according to the invention, so that the instrument (and the gear system thereof formed by the coupling mechanism and the force transmission train thereof, respectively) exhibits non-linear transmission behavior. This means that the ratio of the actuating force of the operating element to the produced closing force of the instrument branches and/or of the actuating travel of the operating element to the effectuated relative positioning (e.g. opening/closing) of the instrument branches is not linear. Preferably, the transmission behavior is such that an initial adjustment travel ($1^{st}$ third-$1^{st}$ quarter) of the operating element (initially meaning starting from the rest position) will result in relatively large relative positioning ($2/3$-$3/4$) of the instrument branches, the ratio will continuously vary in the course of the adjustment travel and a final adjustment travel (last third-quarter) of the operating element (finally meaning shortly ahead of the working position) will result in a relatively small relative positioning ($1/3$-$1/4$) of the instrument branches. Moreover, the transmission behavior may be such that an initial actuating force exerted on the operating element or an initial actuating moment exerted on the operating element, resp., (initial meaning starting from the rest position) will lead to a relatively low resulting force and/or in a relatively low moment of the instrument branches, that the "actuating/closing force" ratio will continuously vary and a final actuating force and a final actuating moment, respectively, (final meaning shortly ahead of the working position) will lead to a relatively high resulting force and/or in a relatively high resulting moment of the instrument branches. The afore-described transmission behavior is achieved by implementing the translating unit (knee lever principle) into the coupling mechanism. The translating unit, on the one hand, is pivotally, especially directly, articulated to the operating element and, on the other hand, interacts with at least one of the instrument branches, at least indirectly via further interposed elements of the coupling mechanism.

In accordance with the invention, the coupling mechanism is (temporarily) biased by means of at least one bias element of the first type. The bias thereof especially into the rest position may cause the instrument branches to be reset from the working position with lower actuating force. By additional bias especially into the working position, the instrument can be provided with a kind of overload protection/travel limitation/force limitation. It is important that the bias element of the first type or the bias elements is/are part of the coupling mechanism and thus is/are disposed in the flux of force thereof. This allows to achieve the advantage, vis-á-vis known instruments, that the bias acts not directly but only indirectly upon the operating element, and thus is also subjected to the transmission behavior of the coupling mechanism. Therefore forces/moments between the bias element and the operating element act with a translation equal/similar to that of forces/moments between the instrument branches and the operating element. The haptic perception in handling the instrument thus is not falsified by the bias thereof. The coupling mechanism may include especially at least two bias elements, with a first one (of the first type) (temporarily) biasing into the working position and a second one (of the second type) (temporarily) biasing into the rest position. For transmitting actuating forces from the operating element to the instrument branches the coupling unit may include especially a tension-compression unit (tension-compression rod) penetrating the shaft portion. Said unit may be formed, for example, from a hollow section (tube) as pressure element and a tension element arranged therein and being axially movable relative thereto (rope/rod). Tension-compression units of this kind are generally known so that a more detailed description in this respect is renounced in the present case.

Thus, the instrument may include a reset support for the user, which does not influence the force finally required for actuating the instrument as intended, however. In particular, the transmission behavior of the instrument can be configured so that the effect of said reset support is more or less weakened or even neutralized in an actuating area relatively close to the working position, while in an area close to the rest position it is reduced only insignificantly or not at all. This facilitates holding (maintaining) the instrument in the working position. It can also be said that the ratio of the restoring force acting on the operating element to the actuating force to be applied by the user to the operating element to overcome the restoring force is smaller in an area close to the working position or in the working position than this ratio is in an area close to the rest position or in the rest position.

Further, the instrument can include an overload protection. The latter can be produced by the bias element (of the first type) or by one of the bias elements having corresponding elastic properties and being integrated in the coupling mechanism. However, it is of particular advantage when the overload protection is produced by the transmission element which, for this purpose, is provided with the appropriately desired elastic properties and forms a kind of spring integrated in the coupling mechanism. According to the invention, the bias element (of the first type) and, resp., the transmission element is not necessarily (permanently) biased. However, it has elastic spring properties. When a certain load is exceeded, especially a limit preset by a bias, by applying force by means of the operating element, the bias element and the transmission element, respectively, will deflect due to its elastic properties. Therefore, further actuation of the operating element is only transmitted indirectly via deformation of the bias element and, resp., the transmission element to the instrument branches and overload of tissue present between the branches and/or overload of other mechanical components of the actuating mechanism can be prevented.

Advantageous embodiments of the invention shall be explained in detail in the following.

One embodiment of the invention is characterized in that the coupling mechanism is biased by a bias element (of the second type), especially a spring element, especially into the rest position, preferably into the open position of the instrument branches. The spring element is arranged on the side of the translating unit facing away from the operating element in the direction of the flux of force. It forms an especially simple and robust mechanism by which the instrument can be provided with a restoring support. The spring element can be in the form of a leaf spring, for example. It is preferably held stationary, on the one hand, relative to the instrument branches, especially supported on the handle element (one leaf spring end is held/fixed on the handle housing) and, on the other hand, it is coupled to the coupling element which is connected to at least one of the two instrument branches via the tension-compression-unit. For coupling to the coupling element, according to one embodiment of the invention, the spring element can have an especially forked seat. The latter is engaged in a coupling contour (undercut/groove) of the coupling element formed for this purpose. The coupling contour may especially be a peripheral groove. The forked seat thus can receive the tension element and, resp., the coupling element in the recess between the fork aims and with the fork aims can engage on both sides in the groove so that force application to the coupling element in a merely axial direction is ensured.

According to one embodiment, the spring element may be biased, especially biased into the rest position while the instrument branches are in the working position or biased into the working position when the instrument branches are in the rest position. In this way, a desired restoring force can be produced which acts not only in the working position of the instrument branches but also close to the rest position or even in the rest position and always safeguards complete restoring of the instrument to the rest position. The bias of the spring element may be adjustable on the user side. For example, for the resilient adjustment of bias of the spring element an additional inserting element, preferably a U-shaped sheet metal, or appropriate reinforcements may be provided.

Another embodiment is characterized in that the translating unit is arranged in the flux of force between the operating element and the spring element. According to the invention, the translating unit is preferably in the form of a knee lever element. Other embodiments of the translating unit are possible and are within the scope of the invention such as a cam unit or a four-bar linkage.

According to one embodiment, the coupling mechanism includes a knee lever element as translating unit. The latter is preferably pivotally articulated directly to the operating element, on the one hand, and interacts indirectly with at least one of the instrument branches, on the other hand, for example via a tension element (strap) of the coupling mechanism adapted to be axially positioned which is coupled to at least one of the instrument branches for positioning them relative to each other. Preferably, the knee lever element, on the one hand, includes a bearing contour for pivotal articulation to the operating element and, on the other hand, includes a coupling portion having two coupling aims formed on both sides of a central recess. In this way, the knee lever element and the coupling mechanism can be coupled on both sides so that actuating forces are applied merely in the axial direction.

It is especially advantageous when the knee lever element which is particularly designed as a sheet metal formed part and/or a sheet metal stamped part has a substantially U-shaped seat for coupling to the spring element. The spring element equally may include a substantially U-shaped coupling recess for coupling to the knee lever element. The spring element and the knee lever element are arranged relative to each other so that the respective coupling recesses thereof engage with each other and permit dynamic coupling with the degrees of freedom required for use as intended. Preferably, the coupling recess of the knee lever element is formed on the inner face of the coupling aims facing the central recess.

A particular embodiment of the invention is characterized in that the transmission element includes a substantially U-shaped spring portion having two opposed spring arms. Via the spring portion the transmission element can be provided especially easily with corresponding elastic properties that are required to produce the already afore-described function of overload protection. Such a spring element is advantageously small, i.e. it requires only little space, is robust and ensures spring characteristics in a direction transversely to the two spring arms, while in the other directions sufficiently high stiffness is guaranteed. It is of particular advantage when the bias of the spring portion can be adjusted by an adjustment screw bracing the spring aims against each other. In this way, the overload protection produced in this way can be adjusted quickly and easily to a specific desired value.

BRIEF DESCRIPTION OF THE DRAWING FIGURES

Hereinafter the invention shall be exemplified in detail by way of drawings, wherein.

Figure 7:
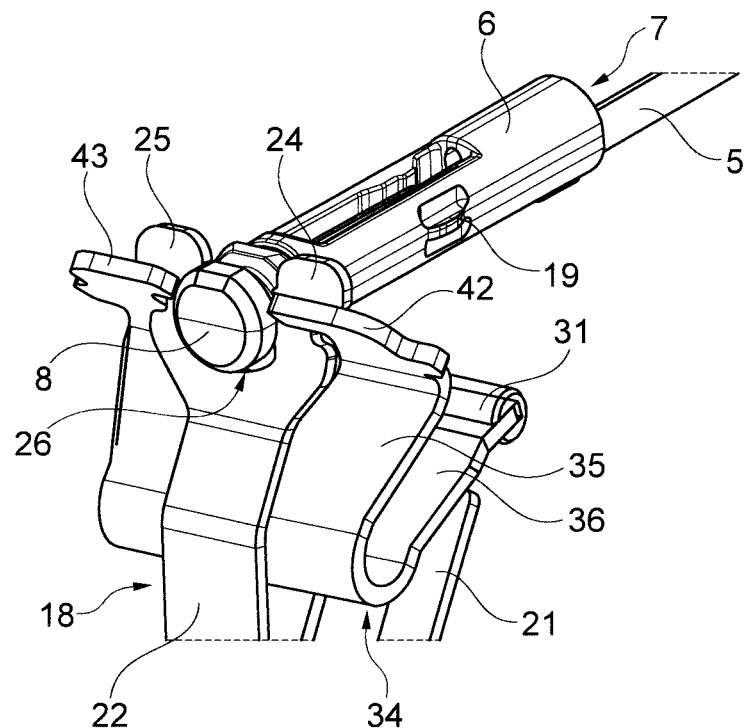
Figure 8:
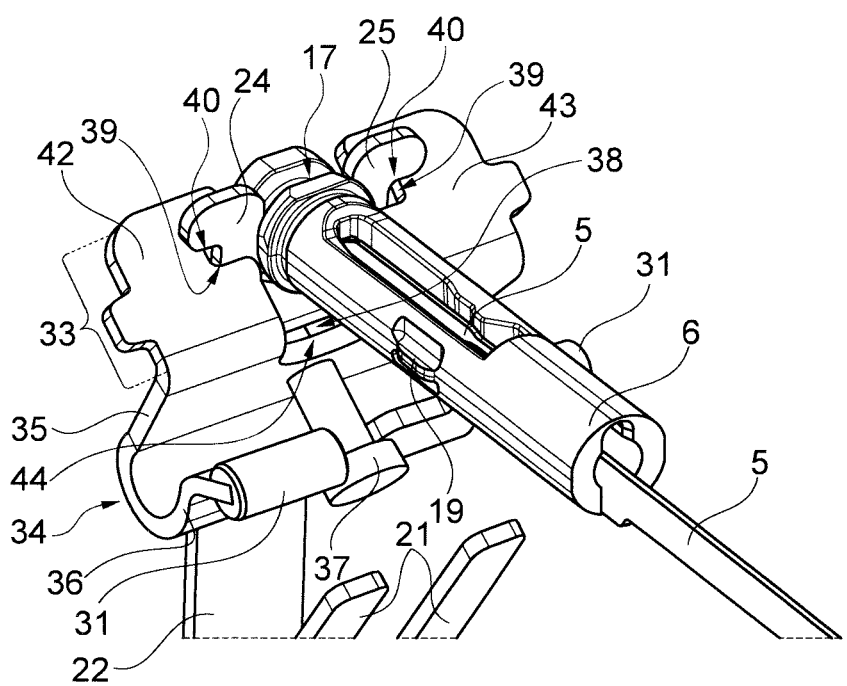
Figure 9:
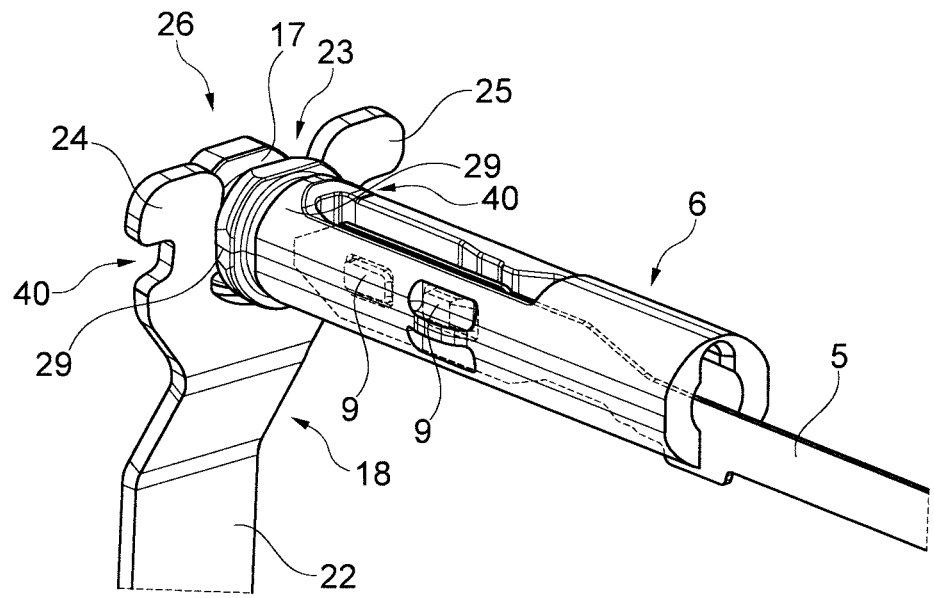
Figure 10:
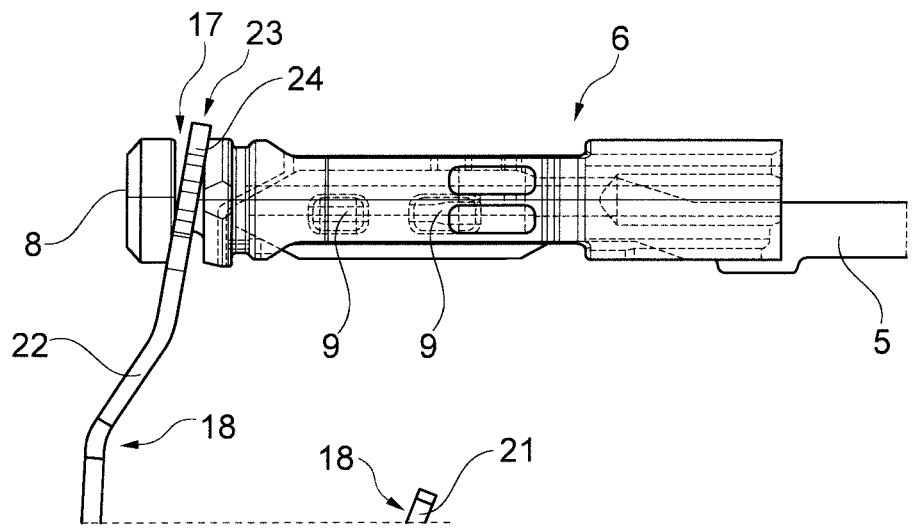
Figure 11:
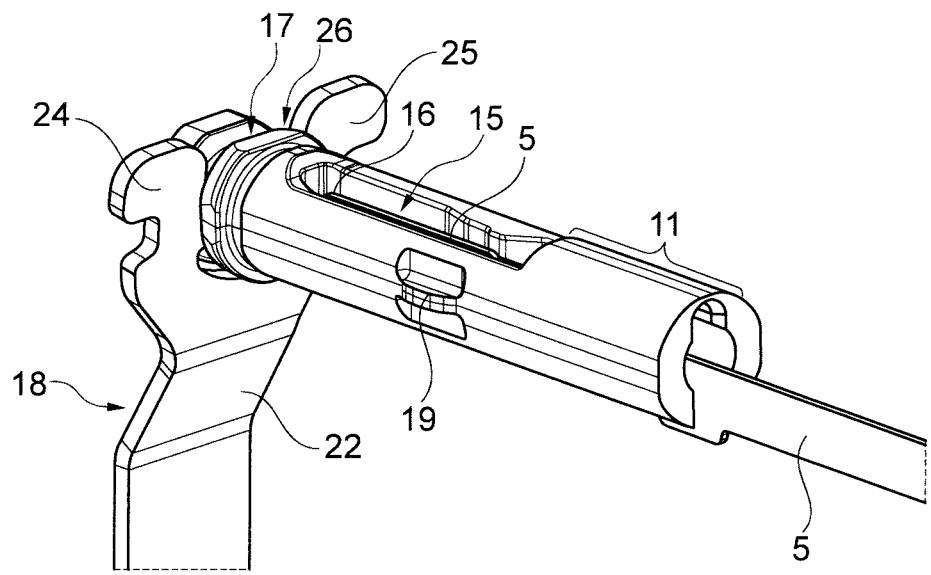
Figure 12:
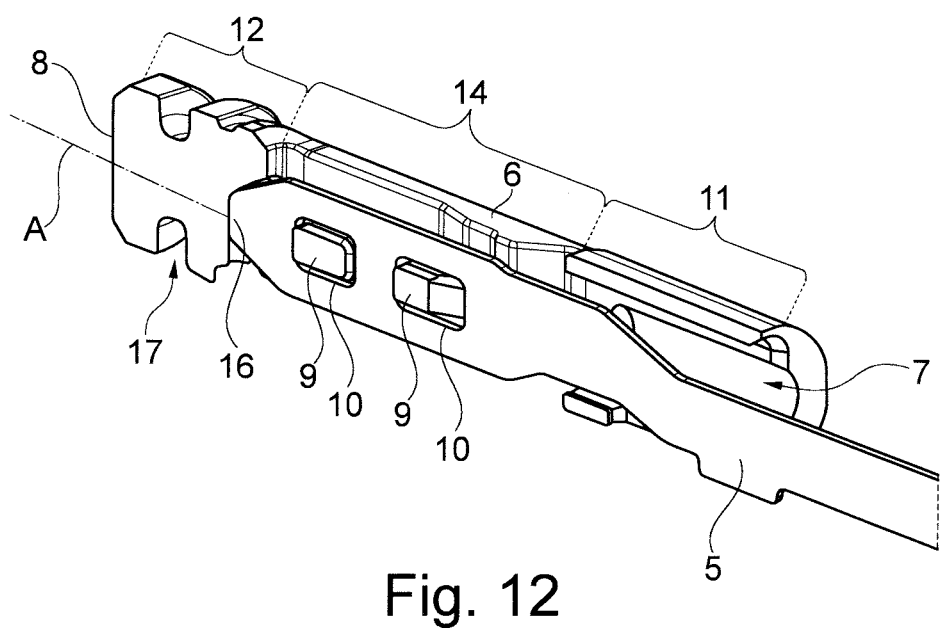
Figure 13:
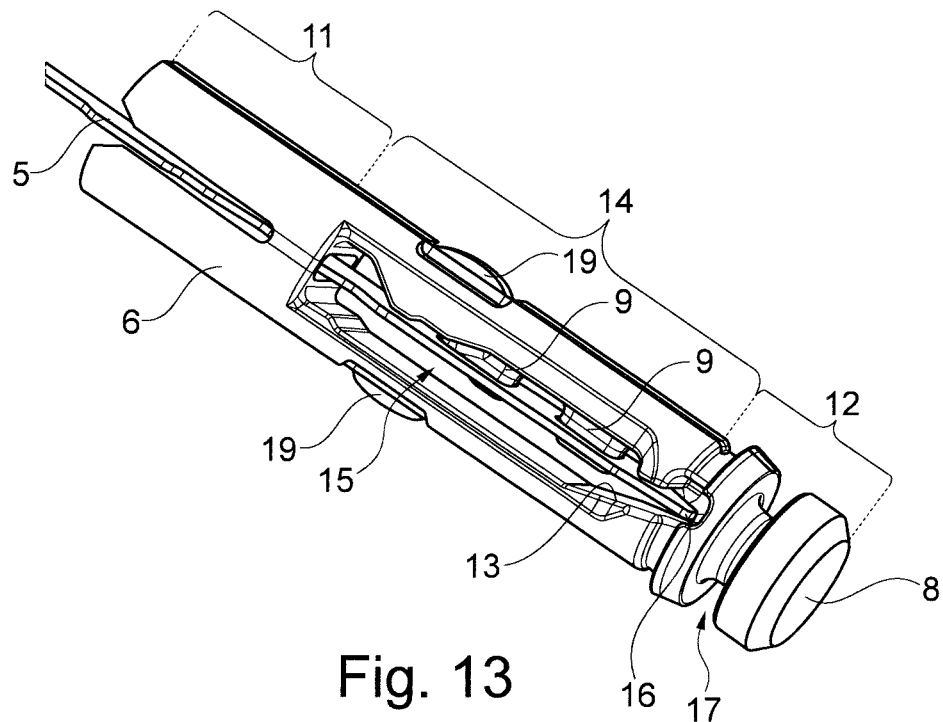
Figure 14:
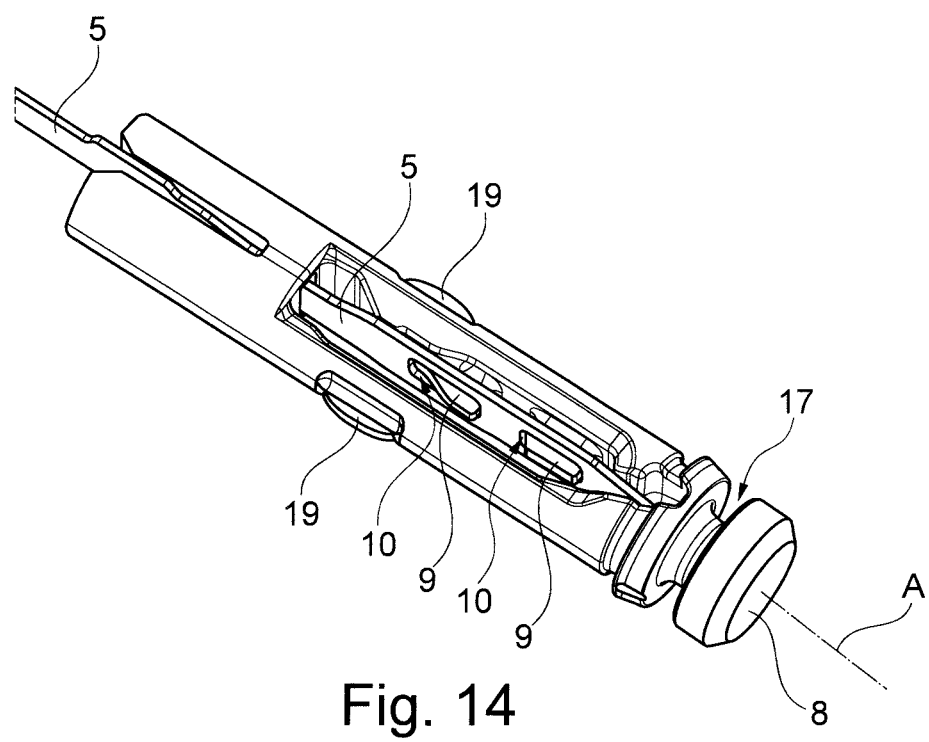
Figure 15:
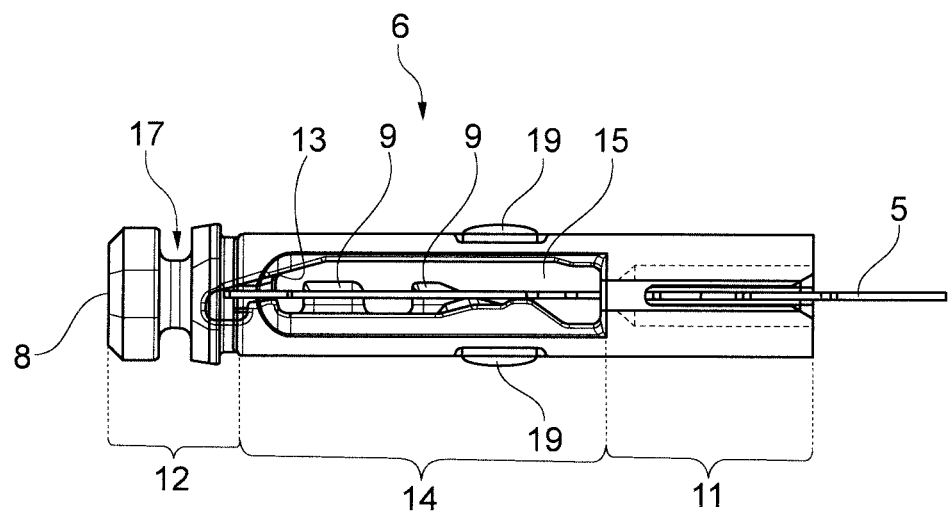

FIG. 7 in a cutout shows a perspective view of part of the coupling mechanism comprising the transmission unit and the spring element;

FIG. 8 shows the cutout from FIG. 7 viewed from a different perspective;

FIG. 9 in a cutout shows a perspective view of part of the coupling mechanism and of the spring mechanism;

FIG. 10 shows the cutout from FIG. 9 in a side view;

FIG. 11 in a cutout shows a perspective view of part of the coupling mechanism;

FIG. 12 shows the cutout of FIG. 11 in a section;

FIG. 13 shows part of the coupling mechanism in a perspective view;

FIG. 14 shows the cutout of FIG. 13 viewed from a different perspective; and FIG. 15 shows the cutout of FIGS. 13 and 14 in a side view.

The drawings are merely schematic and only serve for the comprehension of the invention.

DETAILED DESCRIPTION

The surgical instrument 1 exemplified in the Figures includes a (handle) housing 2 preferably composed of two shells/halves of which the sectional views of FIGS. 1 to 6 illustrate only the inner face of the one/left housing half (when viewed from a person holding the to instrument 1 as intended). The other/right housing half not shown in the Figures is mirror-symmetrical to the left housing half. The housing 2 is configured as/with a handle element/handle portion 3 or handle 3. The proximal side of the instrument 1 is located on the left in FIGS. 1 to 6, the distal side is located on the right. Thus, the handle element 3 is located in a proximal lower area of the housing 2.

Figure 1:
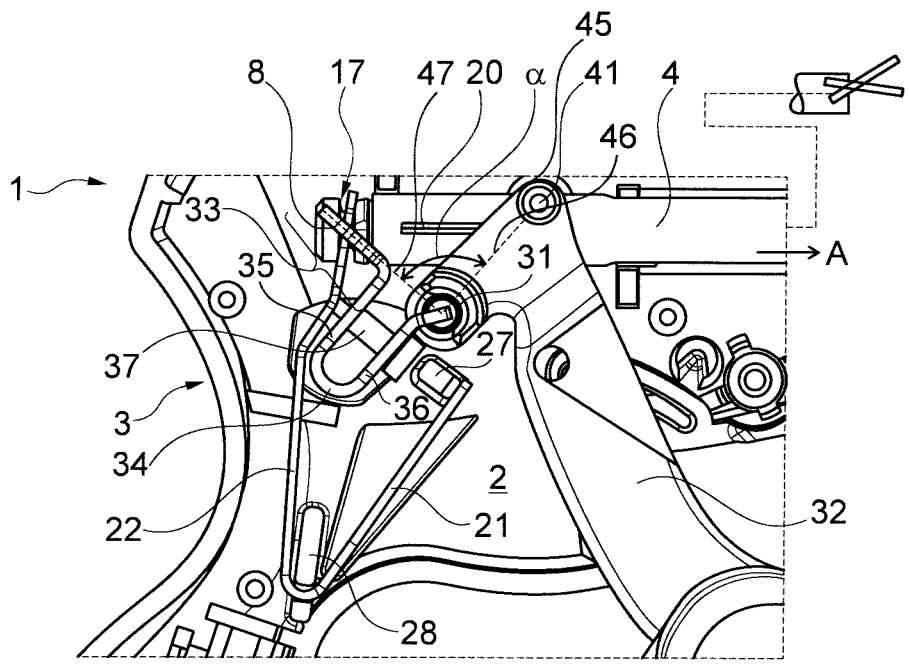
FIG. 1 shows a sectional view of a portion of a surgical instrument according to the invention in a first functional position.

In the (proximal) housing 2 a shaft/instrument shaft 4 is arranged to be fixed in position relative to the housing 2, especially fixed in the axial direction A thereof. The shaft 4 is substantially in the form of a hollow shaft/tube and extends to protrude from the housing 2 in the distal direction (not visible in detail in the Figures). At its distal end not shown in detail in the Figures, the shaft 4 supports two instrument branches which are articulated to the shaft 4 in an axially fixed though pivotal manner. As is evident especially from FIGS. 2, 4 and 6, inside the shaft 4 a tension element 5 e.g. in the form of a strap or Bowden cable is arranged. The tension element 5 can be axially positioned relative to the shaft 4 and is connected, at its distal end not detailed in the Figures, to at least one of the instrument branches. The strap 5 positively engages with its proximal end portion in a coupling element in the form of a coupling sleeve 6 which is equally arranged to be axially positioned inside the shaft 4 in the longitudinal direction thereof, as is illustrated by comparison of the FIGS. 1, 3 and 5 showing different operating positions.

The coupling sleeve 6 is continuously hollow and has a distal open axial end 7 as well as a proximal closed axial end 8. The strap 5 reaches through the open end 7 of the coupling sleeve 6 and is latched to the coupling sleeve 6 in an axially fixed manner via coupling lugs 9 formed inside the coupling sleeve and via coupling openings 10 formed in the strap 5. In order to achieve simple and safe coupling of the strap 5 and the coupling sleeve 6, the coupling sleeve 6 (see especially FIG. 15) includes a distal inner guide portion 11 the inner cross-sectional shape of which substantially corresponds to the outer cross-sectional shape of the strap 5 and in which the strap 5 is laterally supported and guided. A proximal end portion 12 of the coupling sleeve 6 is provided with an inner guiding slope 13 on which the proximal end of the strap 5 in the form of an arrowhead abuts when arranged as intended in the coupling sleeve 6 (see FIG. 15). In a (widened) axial central portion 14 between the portions 11 and 12 the coupling sleeve 6 has a cavity 15 whose width is significantly wider than that of the strap 5 and in which the strap 5 is not guided on the side. Distally the coupling lugs 9 are slanted so that, when the strap 5 is inserted from the distal to the proximal side (from the right to the left in FIG. 15), the proximal end 16 of the strap 5 is deflected from the axial direction A and can be inserted into the coupling sleeve 6 past the coupling lugs 9, until it abuts against the guiding slope 13 and is thus urged back again in the axial direction A, thus causing the coupling lugs 9 to engage and latch in the coupling openings 10. In this way, the strap 5 and the coupling sleeve 6 are coupled in an axially fixed manner.

In the proximal end portion 12 a peripheral outer groove 17 is introduced to the coupling sleeve 6. Said groove serves, as will be described in detail below, for coupling the coupling sleeve 6 to a spring element 18 (bias element of the second type). In its central portion, the coupling sleeve 6 is provided with an outer guide 19 on each of opposite sides, the guides engaging in guide slits 20 formed in the shaft 4 according to the tongue and groove principle, thus causing the coupling sleeve 6 to be held non-rotatably in the shaft 4 but to be supported therein in an axially movable manner.

The spring element 18 in the form of a leaf spring is a substantially U- or V-shaped/bent stamped part made from sheet metal. It has a first spring arm 21 and a second spring arm 22 bent relative thereto. The free end of the second spring arm 22 opposed to the first spring arm 21 is in the form of a forked seat 23 having two fork arms 24 and 25. Between the two fork arms 24, and 25 a central recess 26 is located which (cf. e.g. FIG. 7) is penetrated by the coupling sleeve 6 such that the fork arms 24 and 25 engage in the peripheral groove 17. As is evident from FIGS. 1 to 6, the spring element 18 (in the bending area of its U/V shape) is supported in the housing 2, viz. by the free end of the first spring arm 21 loosely abutting against a bearing bracket 27 forming a fixed bearing point in the housing 2 as well as via a bearing bracket 28 forming a pivot bearing in the kink or, resp., bending/joining area of the two spring arms 21, 22. At each of the respective inner faces of the fork arms 24 and 25, viz. on the side thereof facing the central recess 26, a pin/projection 29 is formed that engages in the peripheral groove 17 to thicken the coupling of the spring element 18 with the coupling sleeve 6. Since the pins 29 have only a relatively small width in the tangential direction to the groove (i.e. in the direction of the respective fork arm 24 and, resp., 25), the spring element 18 can be pivoted about a certain degree vis-á-vis the coupling element 6, which is also resulting from a comparison of the FIGS. 1, 3 and 5.

The coupling mechanism further includes a transmission element 30 in the form of a knee lever element 30. The knee lever element 30 is a sheet metal formed part which is stamped/bent substantially in U shape and which at its one end portion (on the right in FIG. 1) is provided with a bearing contour 31, for example in the form of an eye or a bolt 31. Via the bearing contour 31 the knee lever element 30 is arranged to be relatively pivoting at an operating element 32 which will be detailed below. The knee lever element 30 is configured at its end portion opposite to the bearing contour 31 to form a lever arm 33. Between the lever arm 33 and the bearing contour 31, the knee lever element 30 is formed to have a spring portion 34 (bias element of the first type) including a first spring aim 35 and a second spring arm 36. The spring portion 34 is substantially U-shaped so that the two spring arms 35 and 36 are opposed to each other. The spring portion 34 imparts certain elasticity to the knee lever element 30 so that a kind of overload protection is provided. Excessive load at the instrument branches acts upon the spring portion 34 via the coupling mechanism and results in deflection thereof so that excessive loads are absorbed. The bias of the spring portion 34 can be adjusted by an adjustment screw 37 that penetrates and braces the spring arms 35 and 36 against each other. In other words, the resilient knee lever element 30 is made from a sheet metal strip (leaf spring element) which in cross-section is bent in U/V shape in its central spring portion 34 and in this way forms the two spring arms 35 and 36. At the free end of the one (distal) spring arm 36, the eye or a pivot/hinge bolt/pin 31 is arranged/formed. At the free end of the other (proximal) spring arm 35, a bending of approx. 90° is formed, thus causing the other (proximal) spring arm 35 to expand into the tongue/lug-shaped lever arm 33 that extends in a proximal direction.

The two spring arms 35 and 36 are coupled in their central portions via the bolt-type adjustment screw 37. For this purpose, in the one (distal) spring arm 36 a through-hole is formed and in the other (proximal) spring arm 35 a threaded bore is formed. By screwing in the adjustment screw 37 the two spring arms 35 and 36 can be pressed more or less against each other (above the screw head) and thus the bias of the bow-shaped leaf spring can be adjusted. As is evident especially clearly from FIGS. 7 and 8, in the lever arm 33 a substantially U-shaped seat 38 is formed for positively receiving the spring element 18 in an encompassing manner. The seat 38 substantially consists of two coupling arms 42 and 43 which are arranged on both sides of a central recess 44. In each of the two sides of the coupling arms 42 and 43 of the lever arm 33 facing the seat 38 a coupling recess 39 is configured for (positive) coupling to the spring element 18. A respective coupling recess 40 is formed on each of the two outer faces of the fork arms 24 and 25 of the spring element 18. For coupling the knee lever element 30 and the spring element 18 the coupling recesses 39 and 40 thereof engage with each other in the way especially shown in FIGS. 7 and 8 such that the knee lever element 30 is coupled to the spring element 18 in a relatively pivotable manner and nevertheless force can be transmitted from the leaf spring 34 to the spring 18.

The instrument branches are moved by user-side actuation of an operating element 32. The latter is configured in the form of a trigger and is pivoted—as is resulting from a comparative examination of FIGS. 1 through 6—by means of a bearing structure 41 (pivot bearing/hinge 41) of the housing 2 in the handle element 3. The pivot bearing 41 is configured to be fixed and thus not adapted to be positioned in the housing 2. The operating element 32 further comprises a seat 45 for the bearing contour 31 of the knee lever element 30 as well as a finger or hand opening protruding from the handle element 3 for the user to seize it for actuation.

The operating element 32 and the knee lever element 30 are designed and configured relative to each other such that they form a knee lever mechanism comprising a first knee lever arm 46 formed by the operating element 32 and extending from the pivot bearing 41 thereof to the seat 45 and comprising a second knee lever arm 47 formed by the knee lever element 30 and extending from the coupling recesses 39 thereof to the bearing contour 31 thereof. Ultimately the operating element 32 forms a third lever arm which is oriented substantially at right angles with the first knee lever arm 46 and at its free end defines/has the finger or hand opening.

Figure 2:
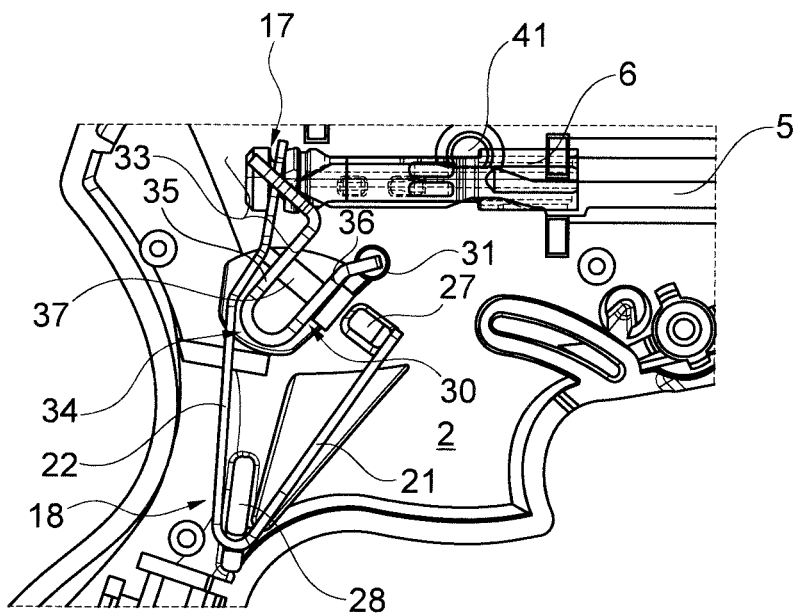
FIG. 2 shows the sectional view of FIG. 1, wherein parts of the instrument are not shown for the purpose of better comprehension.
Figure 3:
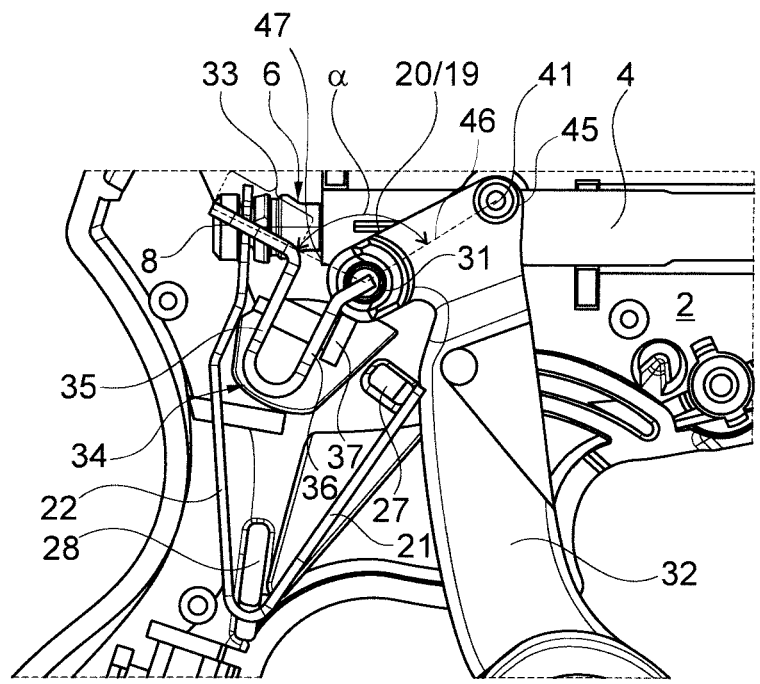
FIG. 3 shows a sectional view of a portion of a surgical instrument according to the invention in a second functional position.

FIGS. 1 and 2 show a sectional view of a portion of the surgical instrument 1 in the rest position as a first functional position in which the instrument branches are open. For better comprehension, in FIG. 2 the operating element 32 and the shaft 4 are not shown. In this position, the coupling sleeve 6 including the strap 5 is positioned in the distal direction (to the right in the Figures) by the action of the spring element 18. The instrument branches are in the idle position and are preferably opened. The two lever arms 46 and 47 of the knee lever mechanism are bent clearly toward each other (knee lever angle $\alpha$ is approx. 90°).

Figure 4:
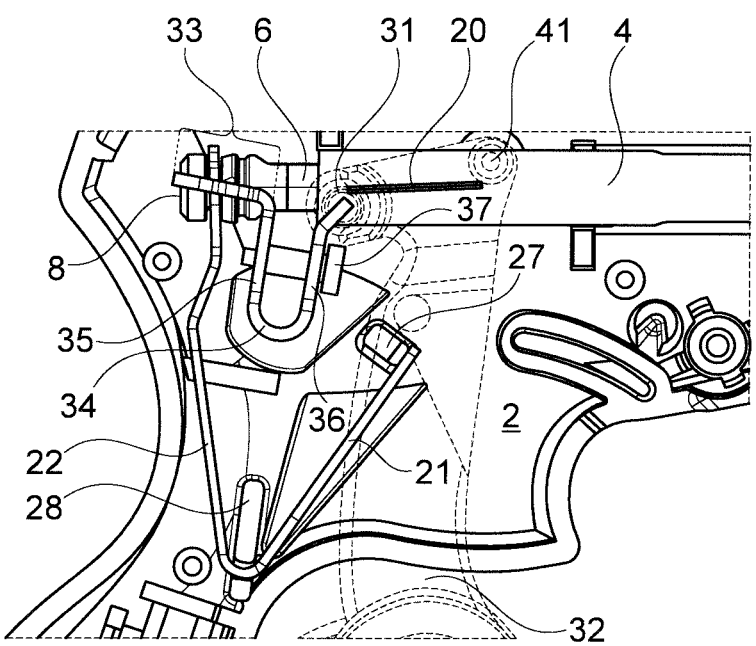
FIG. 4 shows the sectional view of FIG. 3, wherein parts of the instrument are not shown for the purpose of better comprehension.
Figure 5:
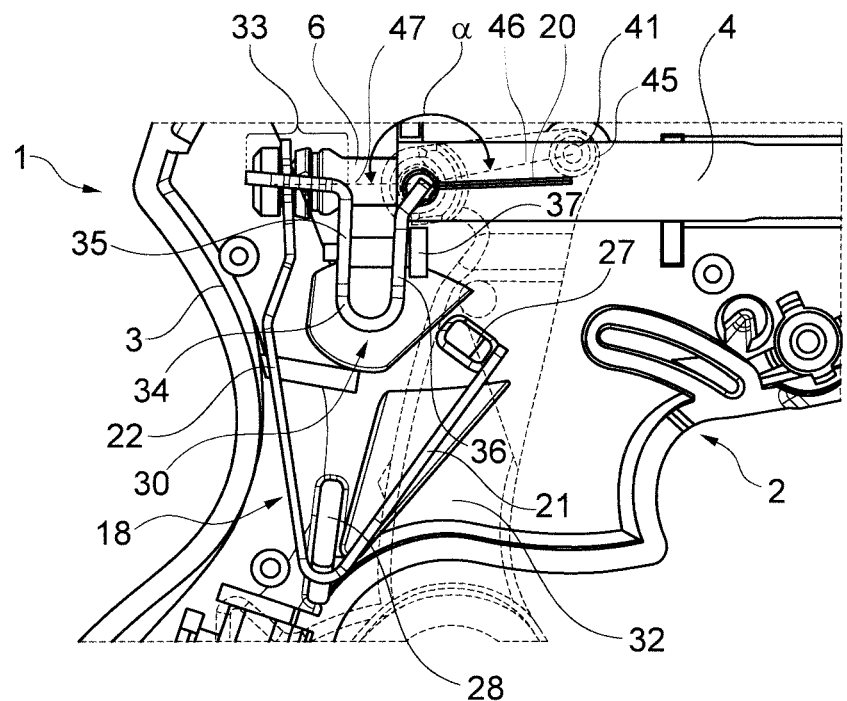
FIG. 5 shows a sectional view of a portion of a surgical instrument according to the invention in a third functional position.
Figure 6:
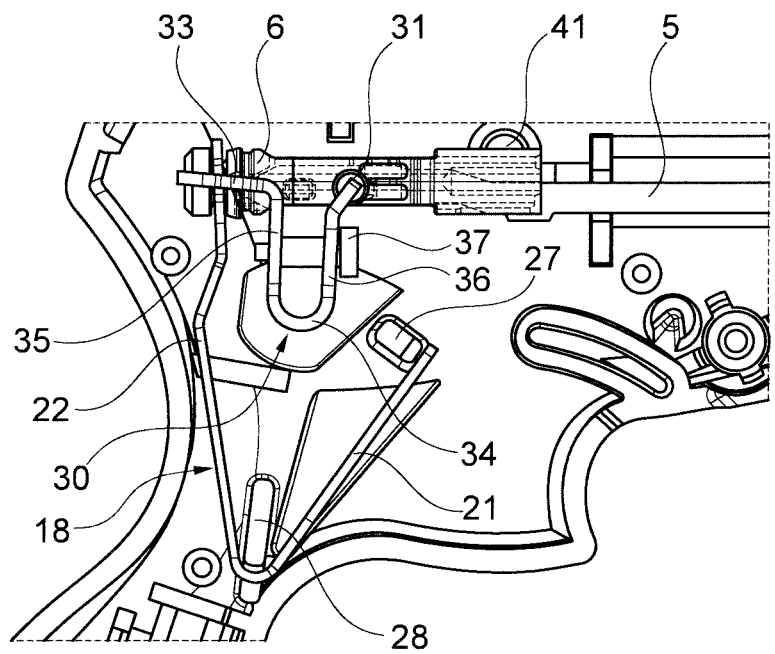
FIG. 6 shows the sectional view of FIG. 5, wherein parts of the instrument are not shown for the purpose of better comprehension.

FIGS. 3 and 4 show sectional views while the instrument is transferred from the first functional position (idle position) shown in FIGS. 1 and 2 to the second functional position (working position) shown in FIGS. 5 and 6. Vis-á-vis the functional position of FIG. 1, the operating element 32 is pivoted already by a certain degree about its pivot bearing 41 toward the handle 3. The lever aims 46 and 47 of the knee lever mechanism are more expanded as compared to FIG. 1 (linearly oriented), the knee lever angle $\alpha$ is larger than in the position of the FIGS. 1 and 2. By expanding the knee lever mechanism a relative positioning (axial displacement) of the coupling sleeve 6 including the strap 5 in the shaft 4 formed to be axially fixed with respect to the handle element 3 in a proximal direction has occurred as compared to the position of the FIGS. 1 and 2. The instrument branches preferably have performed a certain closing movement. It is evident that, due to the angle ratios of the knee lever mechanism present during initial transfer from the rest position (FIGS. 1 and 2) to the intermediate positions of FIGS. 3 and 3, a relatively large translation is given so that the pivoting of the operating element has produced a relatively large displacement of the coupling sleeve 6 and thus of the instrument branches with relatively low force transmission.

FIGS. 5 and 6 illustrate the system after reaching the working position. The knee lever angle $\alpha$ is almost completely straight and amounts to almost 180°. Pivoting of the operating element 32 from the intermediate positions of the FIGS. 3 and 4 to the working position has resulted, due to the angle ratios of the knee lever mechanism given with a relatively large adjusting travel of the operating element 32, only in a relatively small axial displacement of the coupling sleeve 6 in a proximal direction and thus in little change in position of the instrument branches. However, the ratio of the actuating force applied to the operating element 32 by a user to the force acting upon the coupling sleeve 6 (and thus closing force of the instrument branches) is relatively small (i.e. high closing forces can be produced by relatively low actuating forces).

It is clearly visible that shortly before reaching the working position, the overload protection integrated in the knee lever element 30 in the form of the spring portion 34 unfolds its full effect, while deflection of the two spring arms 35 and 36 in the rest position (FIG. 1, 2) is unfavorable due to the angle ratios present in that case. The integrated overload protection therefore unfolds its (full) effect only shortly before reaching the working position and in an adjusting area close to the rest position has only little or no effect (due to friction between and, resp., tilting of the bolt 37 and the spring arm 36) so that there a direct response behavior is given. The force which the spring element 18 inevitably exerts on the operating element 32 (which is to assist restoring of the instrument from the working position to the rest position) is advantageously only transmitted to the operating element to a small extent, almost not at all, in an area close to the working position due to the angle ratios given there, but is transmitted in an adjusting area closer to the rest position. This is of particular advantage, as the user in the working position (or close to the working position) needs to apply no force or only low force to overcome the restoring force of the spring element 18, as the restoring force thereof is applied to the actuating mechanism and the coupling mechanism via the knee lever element 30 as transmission element 30.

The invention claimed is:

1. A surgical instrument comprising:
an instrument shaft;
two instrument branches that are arranged distally thereupon and can be positioned relative to each other in a working position and a rest position;
a handle element on which an operating element is movably arranged for positioning the instrument branches; and
a coupling mechanism having a translating unit that converts a movement of the operating element non-linearly into a relative movement of at least one of the two instrument branches,
wherein the coupling mechanism comprises a first bias element that biases the mechanism into the rest position and/or into the working position of said instrument branches,
wherein the operating element and the first bias element are designed and configured with regard to each other to form a knee lever mechanism of the translating unit in which the first bias element is serially inserted in a force transmission train of the coupling mechanism,
wherein the surgical instrument includes a second bias element that is arranged in parallel to the force transmission train and on a side of the translating unit facing away from the operating element,
wherein the first bias element and the second bias element are positioned proximally with respect to the operating element,
wherein the coupling mechanism is biased into the rest position by the second bias element,
wherein the operating element and the first bias element form the knee lever mechanism in which the operating element has/forms a first knee lever arm and the first bias element has/forms a second knee lever arm which is pivotally coupled to the first knee lever arm to transform a pivoting motion of the operating element into a translating motion having a non-linear translation ratio corresponding to the current angle formed between the first lever arm and the second lever arm, and wherein the first bias element is a leaf spring that is bent in a U or V shape and forms a first spring arm and a second spring arm, the first spring arm being hinged on the first knee lever arm of the operating element and the second spring arm being operatively connected to a coupling element that is connected to at least one of the two instrument branches via a tension element.

2. The surgical instrument according to claim 1, wherein the first spring arm includes a centrally arranged through-/guide hole and the second spring arm includes a centrally arranged screw-thread hole, with a screw bolt including a head being passed through the through-hole and being screwed into the screw hole to resiliently adjust the distance of the first and second spring arms.

3. The surgical instrument according to claim 1, wherein an additional inserting element, or reinforcements are provided for resilient adjustment of the first and second spring arms.

4. The surgical instrument according to claim 1, wherein in the translating unit the first bias element is arranged between the operating element and the second bias element or the second bias element is arranged between the operating element and the first bias element.

5. The surgical instrument according to claim 1,
wherein the second bias element is a compression spring that is supported on the handle element, is coupled to the coupling element connected to at least one of the two instrument branches via the tension element and is articulated, axially relative to the coupling element, to a proximal portion of the coupling element.

6. The surgical instrument according to claim 5, wherein the second bias element includes, for coupling to the coupling element a forked seat which is formed of two fork arms arranged on both sides of a central recess.

7. The surgical instrument according to claim 5, wherein the second bias element is biased, when the instrument branches are in the working position, or is biased into the working position, when the instrument branches are in the rest position.

8. The surgical instrument according to claim 1, wherein the first bias element comprises a bearing contour for pivotable articulation to the first knee lever arm of the operating element and a coupling portion having two coupling arms formed on both sides of a central recess for operative connection with the coupling element to the instrument branches.

9. The surgical instrument according to claim 8, wherein the first bias element comprises, for coupling to the second bias element, a substantially U-shaped coupling recess at each of the coupling arms, and/or in that the second bias element comprises, for coupling to the first bias element, a substantially U-shaped coupling recess.

10. The surgical instrument according to claim 9, wherein the coupling recesses of the first bias element are formed on an inner face of each of the coupling arms facing the central recess.

11. The surgical instrument according to claim 1, wherein the first bias element comprises a bearing contour for pivotable articulation to the first knee lever arm of the operating element and pins for operative connection with the coupling element to the instrument branches.

12. A surgical instrument comprising:
an instrument shaft;
two instrument branches that are arranged distally thereupon and can be positioned relative to each other in a working position and a rest position;
a handle element on which an operating element is movably arranged for positioning the instrument branches; and
a coupling mechanism having a translating unit that converts a movement of the operating element non-linearly into a relative movement of at least one of the instrument branches,
wherein the coupling mechanism comprises a first bias element that biases the coupling mechanism into the rest position and/or into the working position of said instrument branches,
wherein the operating element and the first bias element are designed and configured with regard to each other to form a knee lever mechanism of the translating unit in which the first bias element is serially inserted in a force transmission train of the coupling mechanism,
wherein the surgical instrument includes a second bias element that is arranged in parallel to the force transmission train and on a side of the translating unit facing away from the operating element,
wherein the coupling mechanism is biased into the rest position by the second bias element,
wherein the first bias element and the second bias element are positioned proximally with respect to the operating element,
wherein the second bias element is a leaf spring which is supported on the handle element and is coupled to a coupling element that is connected to at least one of the two instrument branches via a tension element.

13. The surgical instrument according to claim 12, wherein the second bias element includes a first spring arm connected to the handle element and a second spring arm connected to the coupling element, and in that a bending area of the second bias element located between the first and second spring arms abuts on an inner face on a bearing bracket of the handle element.

* * * * *